United States Patent [19]
Benecke

[11] Patent Number: 5,700,276
[45] Date of Patent: Dec. 23, 1997

[54] SURGICAL FORCEPS

[75] Inventor: Rainer Benecke, Todendorf, Germany

[73] Assignee: Olympus Winter & Ibe GmbH, Hamburg, Germany

[21] Appl. No.: 660,485

[22] Filed: Jun. 7, 1996

[30] Foreign Application Priority Data

Jun. 10, 1995 [DE] Germany .......... 195 21 257.6

[51] Int. Cl.$^6$ .................................................. A61B 17/28
[52] U.S. Cl. .............................................. 606/208; 606/206
[58] Field of Search ................................ 606/207, 206, 606/208, 205, 119, 122

[56] References Cited

U.S. PATENT DOCUMENTS 5,147,373  9/1992  Ferzli ................................ 606/207
5,569,299  10/1996  Dill et al. ........................ 606/207

Primary Examiner—Michael Buiz
Assistant Examiner—Kevin Truong
Attorney, Agent, or Firm—Walter C. Farley

[57] ABSTRACT

A surgical forceps assembly for endoscopic and especially arthroscopic interventions has a stem fitted at its distal end with a forceps with a fixed jaw and a pivotable jaw. The stem has at its proximal end an actuator and a force transmitting element passes through and is slidable in the stem. The proximal end of the force transmitting element is connected to and movable by the actuator and the distal end acts on a laterally projecting pin of a lever attached to the pivotable jaw to move the forceps between open and closed positions when the force-transmitting element is axially displaced. The distal end of the force-transmitting element has a coupling with an elongated slot and the lever pin passes through the elongated slot wherein it is received and guided in a cam relationship.

6 Claims, 3 Drawing Sheets

SURGICAL FORCEPS

FIELD OF THE INVENTION

This invention relates to a surgical forceps assembly for endoscopic and arthroscopic interventions with a stem fitted at its distal end with a forceps unit having a fixed jaw and a displaceable jaw, an actuator at the proximal end of the stem, and a force-transmitting element passing through the stem and displaceable relative to it and connected at its proximal end to the actuator, the force-transmitting element engaging a laterally projecting pin of a lever formed on the displaceable jaw so that the forceps unit proper is displaceable between an open and a closed position when the force-transmitting element is displaced axially.

BACKGROUND OF THE INVENTION

As used herein, the term "forceps" will mean the forceps jaws and pivot mechanism itself while the term "forceps assembly" will be used to mean the forceps combined with another mechanism such as an actuating device which is operable from some distance to cause a desired relative movement between the jaws.

Surgical forceps assemblies of this general type having a fixed jaw and a displaceable jaw are particularly useful to remove cartilage or ossified tissue. In the typical case, such forceps assemblies are used during endoscopic arthroscopic interventions such as on the knee.

Such a surgical forceps assembly has a stem at the distal end of which the forceps is fitted with both the fixed and displaceable jaws supported so as to be pivotable about a pivot pin. An actuator is at the distal stem end. Illustratively, the actuator may be a conventional forceps handle with two crossed gripping arms.

A force transmitting element passing through the stem is between the actuator and the forceps proper and may be in the form of a tension wire or a pushrod. The force transmitting element is connected at its proximal end to the actuator which can displace it axially relative to the stem. The distal end of the force transmitting element is connected by a suitable device with the forceps such that, upon axial displacement, the displaceable jaw of the forceps is pivoted.

As a rule, the displaceable jaw has a distal portion constituting a forceps arm and a lever proximally projecting beyond the arm support, the distal end of the force-transmitting element resting, for instance by means of a hinge or pivot pin, on the lever. When the force-transmitting element is axially displaced, the lever is made to pivot and thereby displaces the distal forceps arm commensurately.

A problem arises in that very large forces must be transmitted by arthroscopic forceps assemblies to the displaceable jaw when, for instance, ossified tissue must be removed. Moreover, such forceps assemblies require small diameters and consequently little space is available for the pins in the pivot means and on the lever, as a result of which conventional forceps assemblies can accommodate only limited loads.

When it becomes necessary to cut very hard tissue, the surgeon must apply considerable force to the actuator, such force being transmitted at a ratio typical of such forceps assemblies of 1:4 to 1:6 to the forceps jaws. Overloads may occur, especially with old forceps assemblies, in the region of the pivot and possibly also in the zone where the force-transmitting element is linked to the lever. Consequently, hinge pins in those locations may rupture, and the forceps assembly be destroyed thereby. In particularly serious cases, parts of the displaceable jaw may remain in the knee.

SUMMARY OF THE INVENTION

Accordingly, it is an object of the invention to create surgical forceps assemblies which, while retaining conventional stem size, are less susceptible to destruction and which assure reliable transmission of substantial forces to the displaceable jaw.

The force-transmitting element comprises a special coupling for linkage to the displaceable-arm lever. The coupling of the invention comprises an elongated slot running obliquely to the stem axis and located essentially in a plane parallel thereto, said elongated slot receiving in a sliding manner the laterally projecting lever pin of the displaceable arm. When the coupling is axially displaced in the stem by the actuator drive, the pin guided in the elongated slot is laterally displaced and thereby pivots the displaceable forceps arm. Depending on the orientation of the elongated slot, advancing the coupling may effect either opening or closing the forceps. Depending on the slope of the elongated slot, the magnitude of the transmitted force can be arbitrarily set within design limits.

If the force transmitting element is a longitudinally moved pushrod guided laterally in a tubular element, the coupling essentially will require no further lateral guidance. However, because considerable forces are commonly transmitted, it is preferred that the coupling as well be made safe against sideways rupture. Illustratively, the coupling may be guided in geometrically constrained manner within a zone enclosing the stem, this zone simultaneously also forming the proximal and distal stops if so desired. The pushrod guidance may be achieved by this pushrod resting by its total lateral peripheral surface against the corresponding inside surface of the stem. On the other hand, the pushrod may be supported merely by a portion of its peripheral surface as long as that portion suffices for reliable guidance. The remaining gap between the pushrod and the associated inner stem surface forms a longitudinal inner lumen used, for instance, as a passageway for a fluid rinsing the forceps assembly.

The invention offers a number of advantages. One advantage consists in the pivot shaft and the lever pin now having substantially larger diameters, as called for, than was possible in the state of the art. This feature is available because the forceps assembly of the invention surprisingly allows improved utilization of the space available in the stem. It was found that while keeping the conventional stem cross-section constant, the pivot and the engaging pin can be designed easily with substantially larger diameters (than in the state of the art). The associated increase in strength suffices to adequately channel the forces transmitted to the displaceable jaw and to assure long forceps assembly life. In this respect, the surgical forceps assembly of the invention represents significant improvement over the state of the art.

Couplings with cam controls are already used in surgical forceps assemblies, however they comprise two displaceable jaws contrary to the present invention. The couplings comprise two lateral channels running in opposite directions and guiding the jaws by means of their laterally projecting pins. However, the known forceps assemblies are not designed, nor suitable, for substantial loads. There is the danger in the event of excessive loading that the pins, already suffering from small diameters, may be rotated out of the channels, or ruptured, if the coupling shifts/escapes laterally. This problem is solved in the forceps assembly of the invention by providing, not a channel, but an elongated slot in the coupling, this slot receiving the pin across this slot's thickness with the pin being held on both sides. Therefore, even in the presence of substantial loads, the pin cannot disengage from the coupling and this feature contributes also to the transmission capability of substantial forces to the displaceable jaw of the forceps assembly of the invention.

In a specific embodiment, a pin is on the lever and projects laterally on both sides and is received in a coupling with two mutually aligned elongated slots. This design enhances mechanical strength in the connection zone of coupling and lever.

It is also possible for the lever to have two zones laterally enclosing the coupling in the vicinity of its elongated slot, the pin guided inside the slot being received between those two zones. A pin affixed on both sides in this manner substantially increases mechanical strength.

Further, it is possible to make the elongated slot curved. In this manner the transmission ratio can be advantageously controlled at various forceps aperture angles. On the other hand, it is clearly possible also to make the elongated slot straight. In the latter case the forceps assembly will evince constant force transmission at all forceps aperture angles.

BRIEF DESCRIPTION OF THE DRAWINGS

The invention is described below with reference to the following drawings wherein.

DESCRIPTION OF THE PREFERRED EMBODIMENTS

Figure 1:
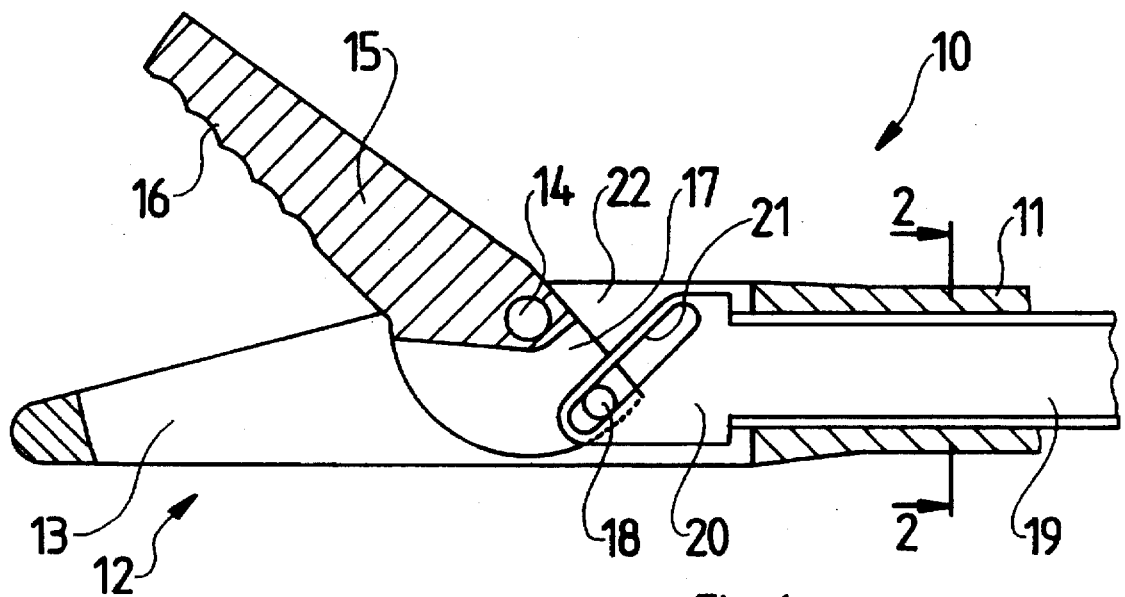
FIG. 1 is a side elevation, in longitudinal section, of the distal zone of one embodiment of a forceps assembly in accordance with the invention.
Figure 6:
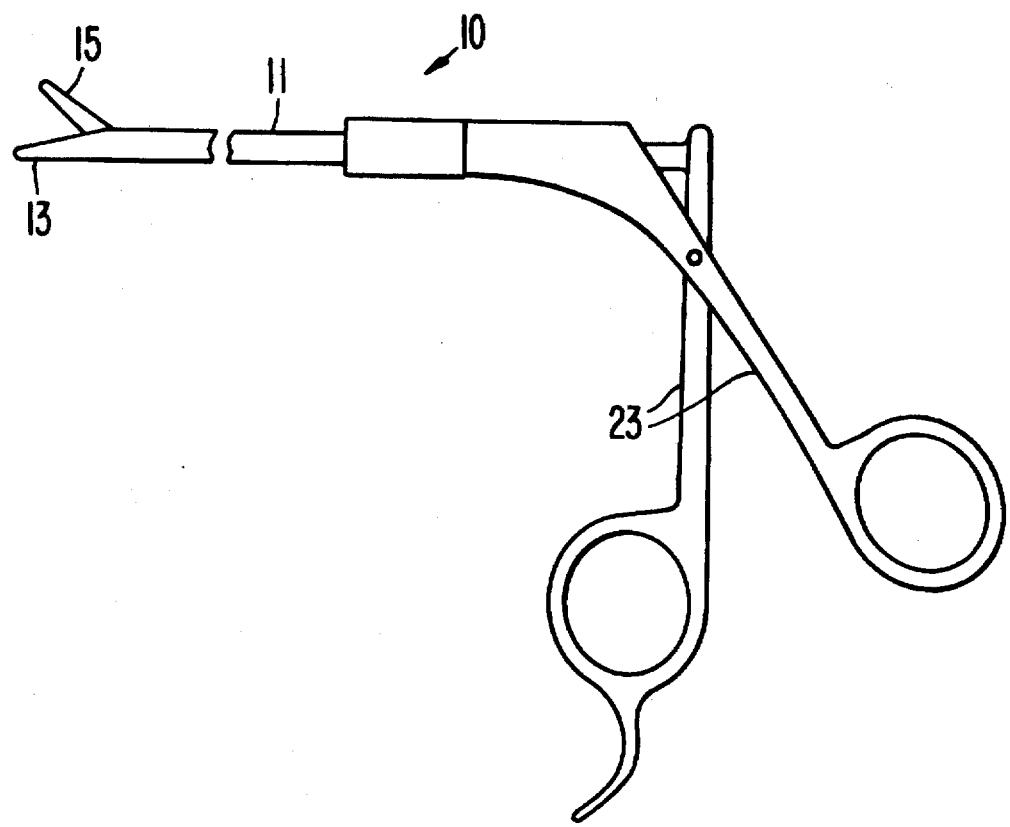
FIG. 6 is a schematic side elevation of a forceps assembly according to the invention.

FIG. 1 is a sectional view showing the proximal end portion of a surgical forceps assembly 10 in accordance with the invention, the overall forceps assembly being shown with somewhat less detail in FIG. 6. Forceps assembly 10 comprise a hollow stem 11 with a longitudinally extending passage therein and a forceps 12 at its distal end. Forceps 12 comprises a fixed jaw 13 and a moveable jaw 15 which is pivotable about a transverse pivot pin 14 relative to jaw 13. By "fixed", it is meant that jaw 13 does not move relative to the stem, while jaw 15 pivots relative to both jaw 13 and the stem. FIG. 1 shows forceps 12 in a partly open state. Displaceable jaw 15 comprises a forceps arm 16 which is distal relative to pivot 14 and a lever 17 which is proximal relative to pivot 14. A guide pin 18 is fixedly attached to, and moveable with, lever 17 and projects laterally from the lever (as illustrated, perpendicular to the plane of the drawing).

Figure 2:
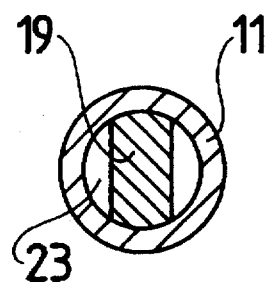
FIG. 2 is a transverse sectional view along line 2—2 of FIG. 1.

The pivoting motion of jaw 15 is implemented by a force-transmitting element 19 which is slidable within stem 11 to actuator handles 23 attached to the proximal end of element 19, the force transmitting element being guided and geometrically constrained within the stem by a portion of its inner surface (also see FIG. 2). As seen in FIG. 6, using actuator handles 23, which are per se conventional, force transmitting element 19 (in this instance a pushrod) can be axially displaced inside the stem.

A coupling 20 at the distal end of force transmitting element 10 couples that element to lever 17 of jaw 15, the coupling including an elongated, sloping slot 21 in coupling 20 receiving guide pin 18. Coupling 20 is partly enclosed by an enlarged cage portion 22 of stem 11. The coupling element can be longitudinally displaced within bail 22 relative to stem 11 and, in the course of this displacement, causes guide pin 18 to travel inside elongated slot 21 and thereby pivots displaceable jaw 15 about pin 14. Starting with the state shown, forceps 12 will be closed when coupling 20 is advanced (moved toward the distal end) and conversely will be opened when coupling 20 is retracted. If the elongated slot 21 were to run in the opposite direction, opening and closing of the forceps 12 would take place in the opposite sense.

The geometrically constrained seating of force transmitting element 19 inside stem 11 reliably prevents element 19 from escaping laterally as it might otherwise when transmitting large forces.

As already indicated, pushrods in particular may be used as force transmitting elements 19 in the forceps assembly of the invention. FIG. 2 shows that when the force transmitting element is in the form of a pushrod, this element rests in a geometrically constrained manner with only a portion of its peripheral surface against the inside of stem 11. This is a preferred embodiment wherein a longitudinal lumen 23 is formed on each side of the force transmitting element and the inside of stem 11. These lumens 23 may advantageously be used to convey fluid to rinse the forceps assembly 10. Alternatively, the entire peripheral surface of force transmitting element 19 may make contact with the inside surface of the stem.

The coupling also can be displaced using a tension wire to close the forceps assembly, opening the forceps automatically for instance using suitable spring systems. But such a mechanism clearly would be more complex. It is therefore preferred that a rigid pushrod be used for force transmission in the forceps assembly of the invention.

Figure 3:
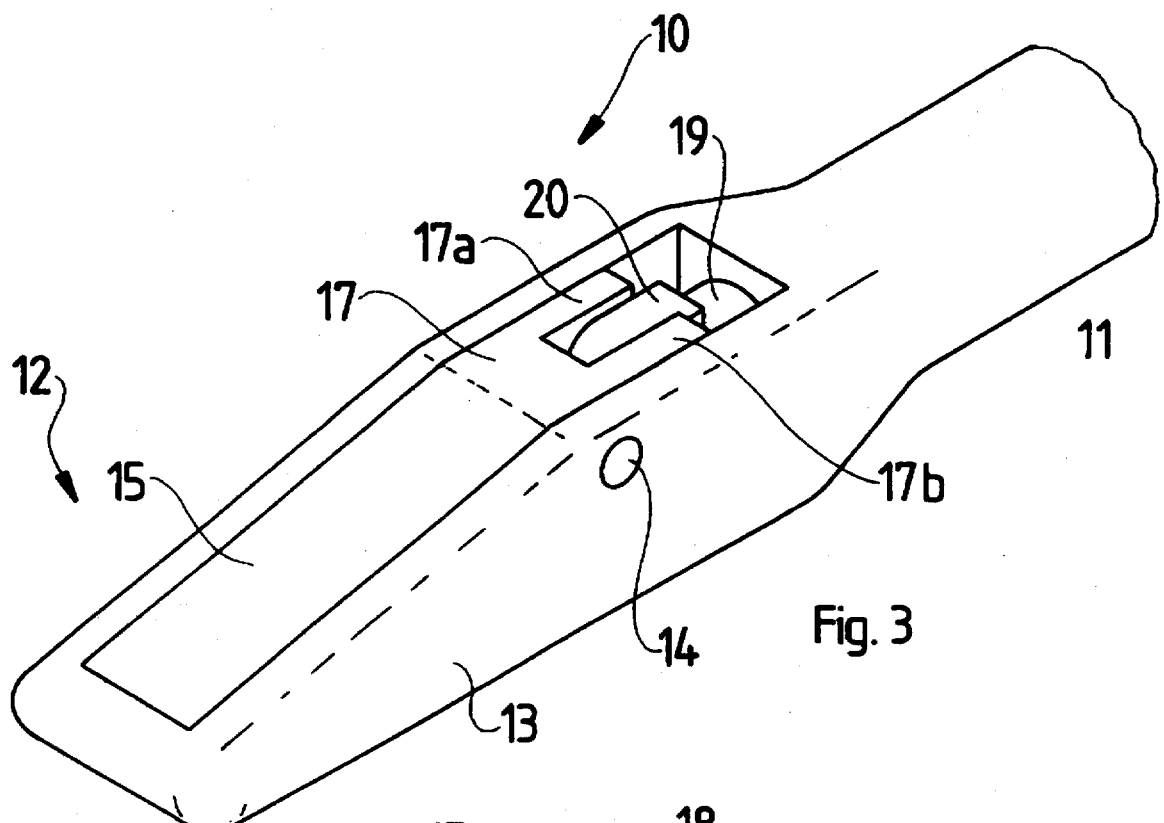
FIG. 3 is a perspective view of the distal end of the forceps assembly of FIG. 1.

FIG. 3 is a partial perspective view of the distal end of a forceps assembly 10 substantially the same as that shown in FIG. 1. Accordingly the same references are used. In this representation, the forceps 12 is shown closed. The figure also shows that the fixed jaw 13 is in the form of a generally U-shaped bail 22 having a hollow interior which entirely receives the forceps arm of displaceable jaw 15 in the closed position of the forceps, whereby bones or ossified tissue can be punched out. The figure also shows pivot pin 14 around which pivots jaw 15. Further, a feature not visible in FIG. 1 is shown, namely, that lever 17 comprises two lateral projections 17a and 17b between which is seated coupling 20.

Figure 4:
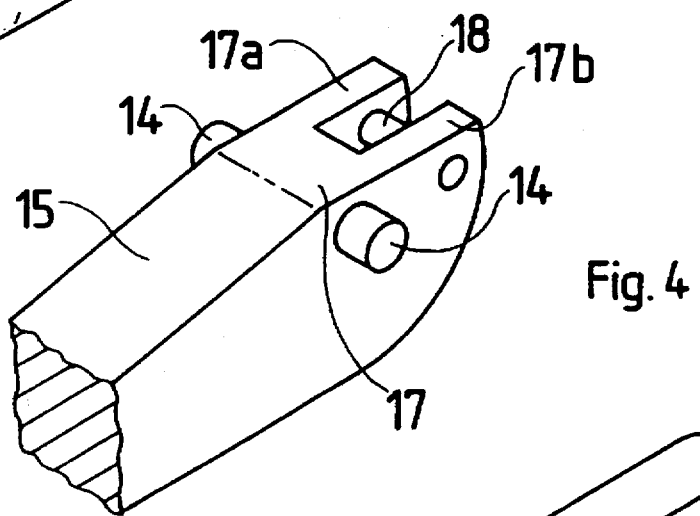
FIG. 4 is a partial perspective view of an embodiment of the displaceable jaw.

Pin 18 extending between projections 17a and 17b and guided in elongated slot 21 of coupling 20 is not visible in FIG. 3 but can be seen in FIG. 4. This view shows displaceable jaw 15 alone. FIG. 4 shows that the pin 18 extends between and is attached to projections 17a and 17b of lever 17.

Figure 5:
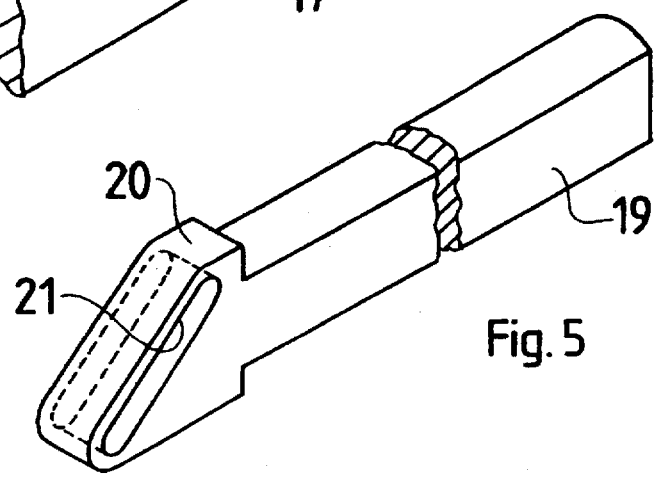
FIG. 5 is a foreshortened perspective view of a first embodiment of an actuating coupling or force transmitting element to be coupled to forceps in accordance with the present invention.

FIG. 5 shows coupling 20 and, in conjunction with FIG. 4, illustrates that the dimensions of the coupling end so match the displaceable arm 15 that the coupling fits into a cavity between projections 17a and 17b and thus receives pin 18 in elongated slot 21, the sides of which are substantially planar.

Figure 7:
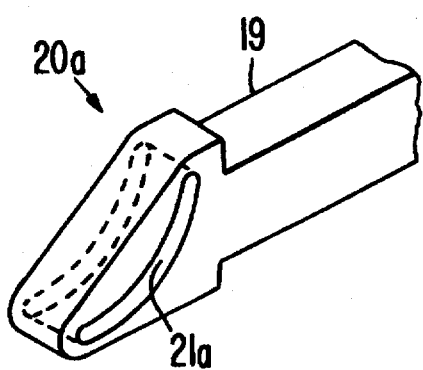
FIGS. 7 and 8 are foreshortened perspective views of additional embodiments of force transmitting elements to be coupled to forceps in accordance with the present invention.
Figure 8:
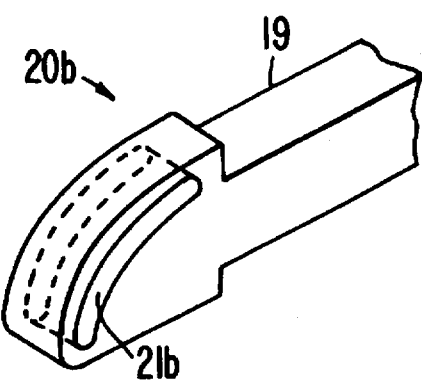

FIGS. 7 and 8 show embodiments of coupling 20a and 20b in which slots 21a and 21b, respectively, are curved rather than straight as in FIG. 5. In FIG. 7, slot 21a is concave as seen from the distal end of the coupling, while in FIG. 8 the slot is convex in the same view. With these curved cam surfaces, the ratio between the force applied by the actuator and the force exerted by the jaws can be made nonlinear to match a wide range of requirements, the two curvatures shown being arranged to provide the strongest force at the end of the stroke in FIG. 7 and at the beginning of the stroke in FIG. 8. It will also be recognized that the curvatures can follow a path which is circular or non-circular.

As already discussed above, the invention is not restricted to the embodiments shown. Other structural arrangements for the coupling, the force-transmitting element and the elongated slots are conceivable. For instance, and as already mentioned above, a coupling with two aligned elongated slots may be used, the lever of the displaced arm with two laterally projecting pins being mounted between said slots. Obviously too the lever of the displaced jaw may enter only unilaterally an elongated slot of a coupling. In these respects, no limits are placed on possible implementation.

What is claimed is:

1. A surgical forceps assembly for endoscopic and arthroscopic interventions, comprising a stem (11) having a longitudinal, axially extending passage therein;

a forceps (12) at a distal end of said stem, said forceps comprising a first jaw (13) fixedly carried by said stem and a second jaw (15) pivotably mounted on said stem;

actuator means (23) at a proximal end of said stem;

a force transmitting element (19) passing axially through said stem, said force transmitting element being displaceable along a central longitudinal axis of said stem and connected at a proximal end to said actuator means;

a coupling (20) at a distal end of said force transmitting element, said coupling comprising an elongated slot (21) extending obliquely to the axis of said stem (11); and said second jaw (15) including an actuating lever comprising two projections (17a, 17b) defining a cavity receiving said coupling (20) and said elongated slot (21), and a pin (18) extending between said projections, opposite ends of said pin (18) being attached to said projections (17a, 17b) and laterally projecting into said elongated slot (21) in a sliding relationship, said pin and slot forming a cam drive whereby, when said force transmitting element is displaced axially, said actuating lever is pivoted to move said second jaw toward and away from said first jaw between open and closed positions.

2. A surgical forceps assembly according to claim 1 wherein said projections (17a, 17b) laterally enclosing said coupling (20) are parallel with each other.

3. A surgical forceps assembly according to claim 1 wherein said elongated slot (21) is arcuate.

4. A surgical forceps according to claim 1 wherein said force-transmitting element (19) is a pushrod guided in said stem axially extending passage and geometrically constrained against movement transversely to said axis.

5. A surgical forceps assembly according to claim 1 wherein a portion of a peripheral surface of said force-transmitting element (19) is guided inside said stem (11).

6. A surgical forceps assembly according to claim 1 wherein said first jaw comprises a generally U-shaped bail enclosing said second jaw in said closed position.

* * * * *